United States Patent [19]

Gorman, Jr. et al.

[11] 4,431,506

[45] Feb. 14, 1984

[54] APPARATUS FOR GEL ELECTROPHORESIS

[75] Inventors: William W. Gorman, Jr.; Esther M. Gorman, both of St. Petersburg Beach, Fla.

[73] Assignee: E-C Apparatus Corporation, St. Petersburg, Fla.

[21] Appl. No.: 415,379

[22] Filed: Sep. 7, 1982

[51] Int. Cl.$^3$ .......................... B01D 13/02; C25B 7/00
[52] U.S. Cl. ...................... 204/299 R; 204/180 G
[58] Field of Search ...................... 204/299 R, 180 G

[56] References Cited

U.S. PATENT DOCUMENTS 3,208,929  9/1965  Raymond et al. ............... 204/299 R
3,374,166  3/1968  Raymond ........................ 204/299 R
3,407,133  10/1968  Oliva et al. ..................... 204/299 R
3,715,295  2/1973  Tocci ............................... 204/180 G
3,980,540  9/1976  Hoefer ........................ 204/299 R X Primary Examiner—G. L. Kaplan
Assistant Examiner—Nam X. Nguyen
Attorney, Agent, or Firm—Bernard, Rothwell & Brown

[57] ABSTRACT

Vertical gel electrophoresis apparatus of the type wherein the gel is cast in a horizontal position using an extending top wall to define an end of the casting chamber, is improved by making the top wall removable to allow access to sample slots in the gel from directly overhead and to provide for attachment of a syringe holder at the position of the removed wall.

4 Claims, 5 Drawing Figures

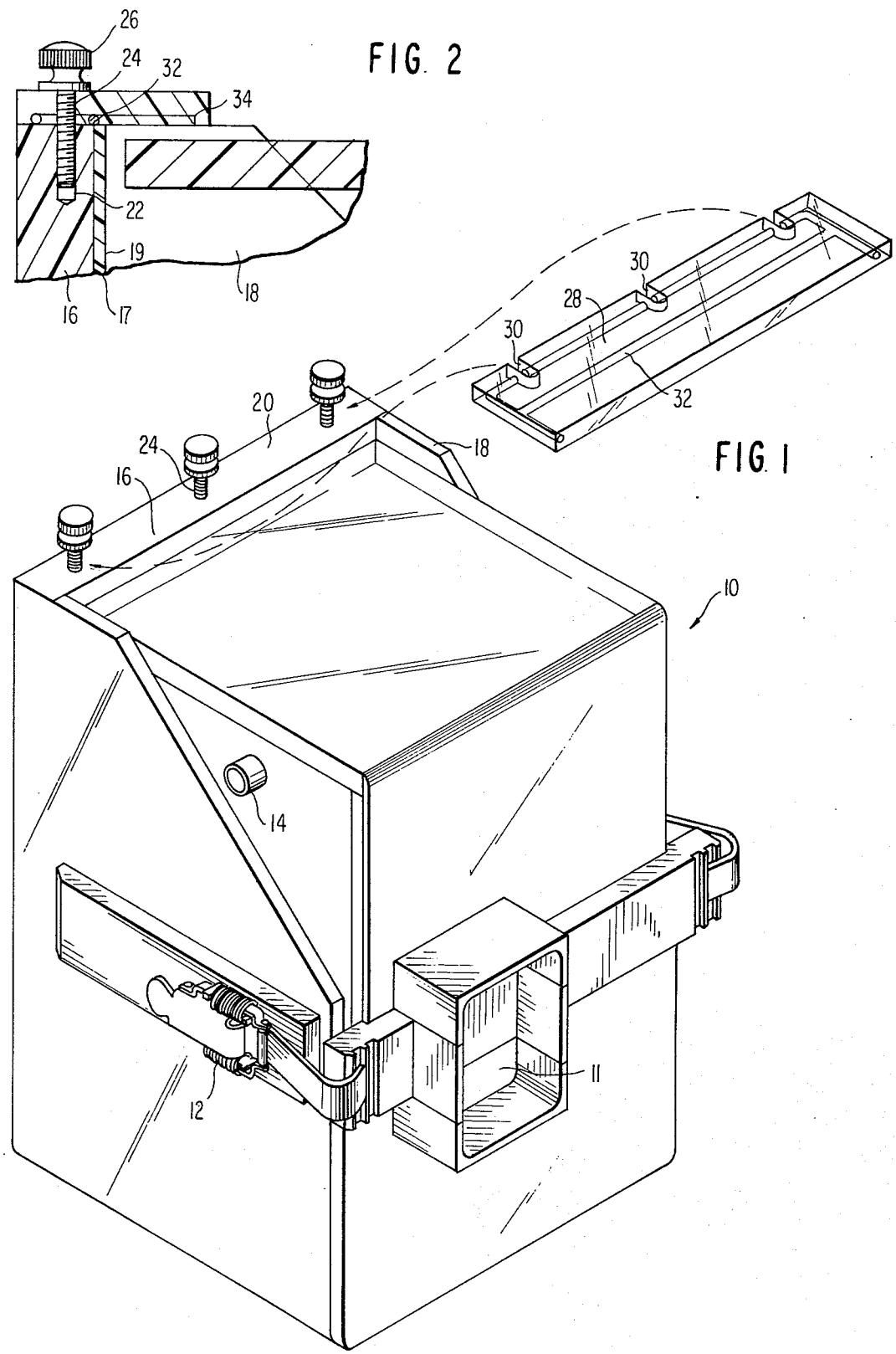

APPARATUS FOR GEL ELECTROPHORESIS

BACKGROUND OF THE INVENTION

1. Field of the Invention

This invention relates to improvements in apparatus for gel electrophoresis, and particularly to an improved vertical gel electrophoresis apparatus.

2. Prior Art

Vertical gel electrophoresis apparatus were first introduced in about 1960. Vertical gel electrophoresis systems now offer laboratory scientists a fully developed and advanced separation technology. They are flexible with regard to the gel media systems, complete and easy to use for analytical and preparative work, and there is substantial documentation in the form of published methodology. Vertical gel electrophoresis systems are utilized for simple to complex separations. They handle proteins, enzymes, hormones, nucleic acids, plant proteins and various tissues. The separations may be analytical in form where the final results are detected by staining, incubation, or radioactive detection. For preparative separation the gel slab is further processed to extract or elute the separated fractions.

Vertical gel electrophoresis apparatus are shown in prior U.S. Pat. Nos. 3,208,929 and 3,374,166. As taught in these patents, and as practiced in the laboratories, the apparatus is assembled and the gel slab is prepared by casting it with the normally vertical gel passageway in a horizontal position. See FIG. 2 of the '929 patent. In casting, a top wall (see wall 45 of the '166 patent or wall 17 of the '929) is utilized to form an end of the casting tray.

After the gel is cast and the apparatus is put in operation with the gel slab in its normal vertical position, this short top wall presents certain operational difficulties. Specifically, the addition of sample to preformed slots in the top of the gel was made tedious by lack of direct access to the gel from above. There was also no simple or easy means to hold a syringe to place the sample and such had to be done tediously and manually.

SUMMARY OF THE INVENTION

This invention overcomes the difficulties and problems of the prior art enumerated above by providing a removable plate which forms the end wall for casting the gel in place of the top short wall in the electrophoresis apparatus of the prior art. The removable plate is clear plastic and suitably gasketed and allows the user the ability to observe air bubbles between the cooling plates in the liquid gel material so that they may be removed before the gel becomes solid with air bubbles trapped which could cause distorted results. More importantly, however the clear gasketed plate can be removed after the gel is formed to allow access to the sample slots in the gel from directly overhead. This makes it much easier to insert the samples for the electrophoresis separation.

Additionally, a syringe holder with preformed spaced holes for positioning syringes may be placed on top of the electrophoresis apparatus in place of the top wall and when so placed the syringes will automatically be positioned directly above the sample slots, so that the sample slot injection can take place directly and easily.

BRIEF DESCRIPTION OF THE DRAWINGS

FIG. 1 is a perspective view of the apparatus of this invention.

FIG. 2 is a detailed sectional elevation view of the apparatus of this invention.

DETAILED DESCRIPTION OF THE PREFERRED EMBODIMENT

Figure 3:
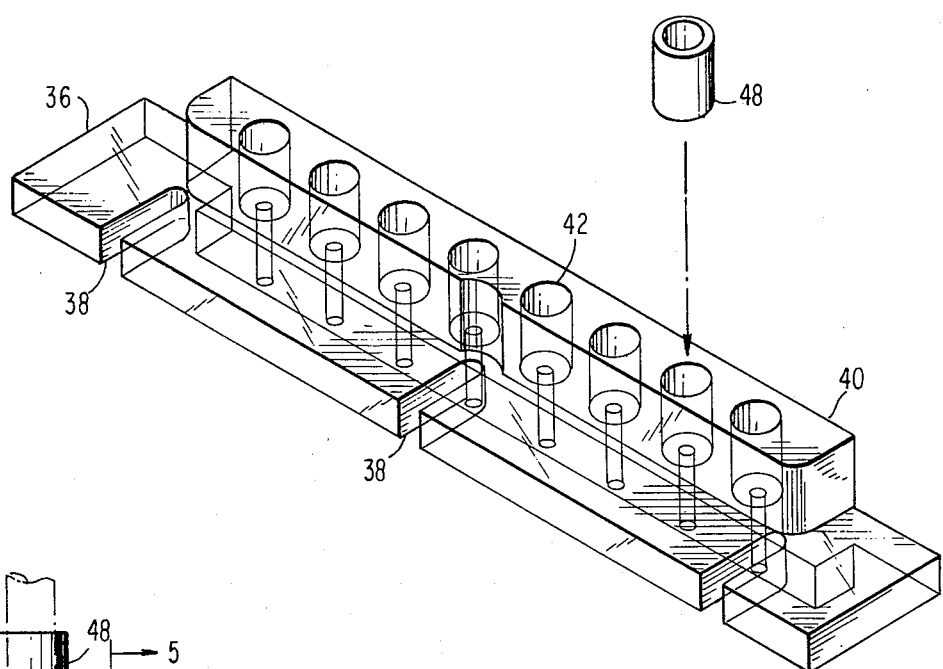
FIG. 3 is a perspective view of a syringe holder forming a part of this invention.

A vertical gel electrophoresis apparatus 10 may be of the general type as shown in U.S. Pat. Nos. 3,208,929 and 3,374,166 or that commercially available from E.C. Apparatus Corp. in St. Petersburg, Fla. As is known in the art, and therefore need not be shown herein, such apparatus includes a lower buffer solution chamber capable of holding liquid buffer solution, an upper buffer solution chamber capable of holding liquid buffer solution, a wall of each buffer solution chamber defining a gel passageway which gel passageway is in fluid communication with the liquid buffer solution of the buffer solution chambers. When the passageway is filled with impermeable gel, free flow of buffer solution from the upper chamber to the lower chamber is prevented by the gel. The apparatus has an electrode in each buffer solution chamber positioned below the normal level of buffer solution therein and the electrodes are connected to a source of DC current through connectors positioned in connector block 11. The upper and lower solution chambers and the gel passageways are constructed of electrically insulating material such as clear plastic. The apparatus has means for holding the upper and lower buffer solution chambers in rigid assembled relationship such as spring biased toggle clamp 12.

In the known prior art apparatus there is also an overhanging top wall which functions as an edge for a tray for casting the gel and the gel passageways when the apparatus is put in a horizontal position when casting the gel slab. See, for example, short wall 17 in prior patent 3,208,929 and its function is shown in FIG. 2 with the gel slab being cast in the horizontal position.

The electrophoresis apparatus of this invention has the same general components in the prior art as described above including the connector 14 for buffer solution circulation and a back wall 16 having a surface 17 on which the gel slab is cast. There are side walls 18 extending from back wall 16. Spacers 19 which can be of varying thickness, space the walls of the gel passageway and determine the thickness of the gel slab to be cast.

Rather than having a top wall as in the prior art, back wall 16 has a flat top 20 in which there are three threaded holes 22. These holes accommodate attaching screws 24 having knurled heads 26. A removable clear plastic plate 28 as shown in FIGS. 1 and 2 is provided with three slots 30 corresponding to the position of the screws 24. One surface of the plate has a gasket 32 in a groove 34 to seal the plate 28 along the top 20 of the back wall 16 and the top of the side walls 18.

As shown in FIG. 1 the clear plate 28 is removable and is initially positioned with the slots 30 around the threaded portion of screws 24. The screws are then tightened to position the plate 28 as shown in FIG. 2 where it can function as the end of a tray for casting the gel. After the gel is cast the plate 28 can be removed for insertion of the sample into the gel. This sample can be inserted into sample slots formed in the gel by sample slot formers of the type known in the prior art.

The clear plastic plate 28 allows the user the ability to observe air bubbles in the liquid gel material as it is being cast so they can be removed before the gel becomes solid with the air bubbles trapped which could cause distorted results.

In operation of casting the gel the clear plastic gasketed plate 28 is affixed to the top 20 of the back wall 16 (which wall is the outer cooling plate). The cell is tipped slightly and gel solution is poured between the cooling plates, i.e. onto surfaces 17 of back wall 16. The cell is laid horizontally and a small excess of gel solution is added to insure the gel area is completely filled. If air bubble(s) are observed through the clear end plate the cell is tipped to allow the bubble(s) to escape or be swept into the open area by the liquid wave caused by lowering the cell in the horizontal position. With the cell in the horizontal position and the gel still liquid (prior to polymerization or solidification) a slot forming template is selected and placed between the cooling plates to form either an area for stacking gel or the sample slots. Other arrangements for forming gel as known in the art may be used.

After gel formation the cell is placed in the vertical position, the tubing connections are made, and the cell is filled with buffer in both the upper and lower compartments to their appropriate levels. The buffer is added prior to removal of the sample slot former so that the when the slot former is removed the preformed slots will fill with buffer rather than air which would prevent proper filling later. Access to the slot former area is aided by removal of the gasketed end plate 28 from the top of outer cooling plate or back wall 16.

Figure 4:
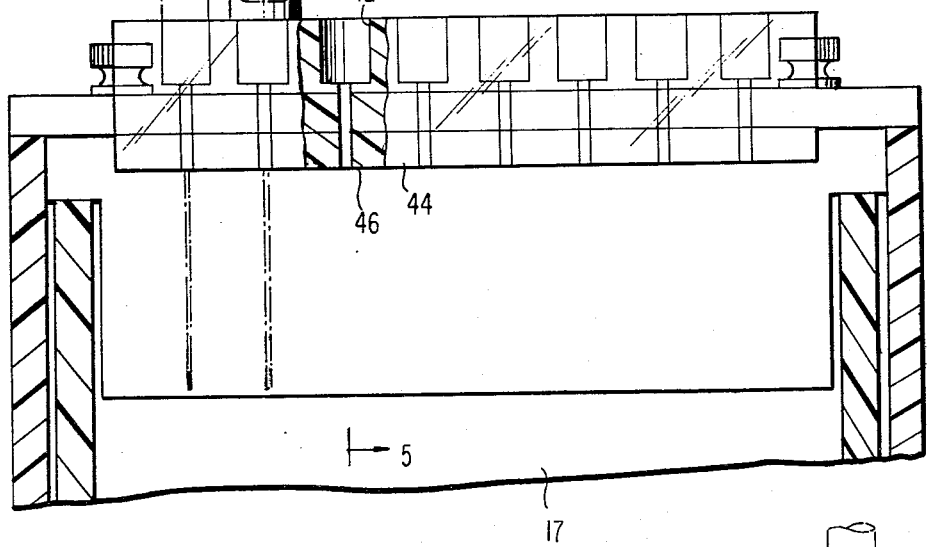
FIG. 4 is an end view partially in section of this syringe holder installed on the apparatus of FIG. 1.
Figure 5:
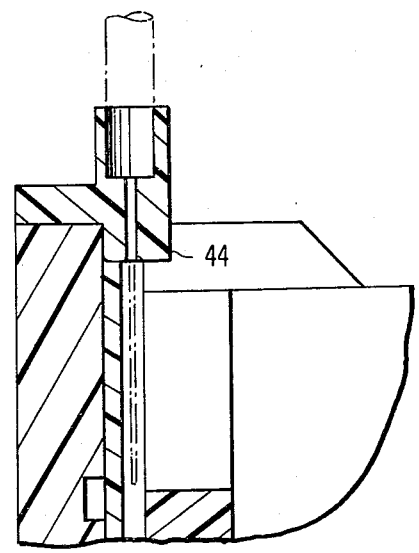
FIG. 5 is an sectional view taken along line 5—5 of FIG. 4.

Samples may be added to the preformed slots, or directly to gel without preformed slots, by placing a syringe directly above each slot and slowly expelling the sample. To aid in sample addition a syringe holder shown in FIGS. 3-5 is provided. This syringe holder 36 has three slots 38 similar in position to slots 30 on gasketed end plate 28. A syringe holding block portion 40 has a plurality of cylindrical syringe holding holes 42 positioned therein. A depending portion 44 has syringe needle holes 46 concentric to the holes 42 as shown in FIGS. 3-5.

A spacer 48 is provided so that different types of commercially available syringes may be utilized in the same syringe holder. The spacer is a cylindrical piece of plastic which fits on the bottom of the syringe and therefore positions the syringe needle at the correct position in the gel.

The use of the syringe holder greatly facilitates the addition of samples and assures that the samples are correctly positioned with regard to the gel or any slots in the gel.

The apparatus as a whole and particularly the improvements herein speed up the preparation for electrophoresis including casting the gel and inserting the sample by a simple, uncomplicated and novel construction.

We claim:

1. A vertical gel electrophoresis apparatus of the type including a lower buffer solution chamber capable of holding liquid buffer solution, an upper buffer solution chamber capable of holding liquid buffer solution, a wall of each buffer solution chamber defining a gel passageway, the gel passageway being in fluid communication with the liquid buffer solution and the buffer solution chambers, and when the passage is filled with impermeable gel free flow of buffer solution from the upper chamber to the lower chamber is prevented by the gel, an electrode in each buffer solution chamber positioned below the normal level of buffer solution therein, each electrode including means for connection to a source of direct current, the upper and lower solution chambers and the gel passageways being constructed of a material having electrically insulating properties at least on the surface thereof, means holding the upper and lower buffer solution chambers in rigid assembled relationship, and an overhanging top wall which functions on an edge for a tray for casting the gel in the gel passageways when the assembled apparatus is in a horizontal position, with the improvements comprising: means for removably securing the overhanging of a top wall in fluid tight relationship to allow removal of the top wall after casting the gel so that the sample may be introduced vertically into the gel from above, and a removable syringe holder, the syringe holder being of a shape to be attached to the electrophoresis apparatus in the position of the removable top wall with syringes to be carried thereby having their needles directed vertically into the gel for the insertion of sample into the gel electrophoresis.

2. A vertical gel electrophoresis apparatus of the type including a lower buffer solution chamber capable of holding liquid buffer solution, an upper buffer solution chamber capable of holding liquid buffer solution, a wall of each buffer solution chamber defining a gel passageway, the gel passageway being in fluid communication with the liquid buffer solution and the buffer solution chambers, and when the passage is filled with impermeable gel free flow of buffer solution from the upper chamber to the lower chamber is prevented by the gel, an electrode in each buffer solution chamber positioned below the normal level of buffer solution therein, each electrode including means for connection to a source of direct current, the upper and lower solution chambers and the gel passageways being constructed of a material having electrically insulating properties at least on the surface thereof, means holding the upper and lower buffer solution chambers in rigid assembled relationship, and an overhanging top wall which functions on an edge for a tray for casting the gel in the gel passageways when the assembled apparatus is in a horizontal position, with the improvements comprising: screw means for extending through the overhanging top wall into the wall defining the gel passageway for removably securing the overhanging top wall in fluid tight relationship to allow removal of the top wall after casting the gel so that the sample may be introduced vertically into the gel from above, the overhanging top wall being formed of clear plastic, gasket means to provide the fluid tight relationship, the gasket means shaped and positioned to seal the side of the removable top wall to the top of the wall defining the gel passageway while allowing visibility of the gel through the clear plastic top wall.

3. A vertical gel electrophoresis apparatus of the type having a pair of cooling plates defining therebetween a passageway for casting gel in the horizontal position, further comprising a clear plastic gasketed end plate, means for positioning the end plate at the top of the outermost cooling plate and securing it in fluid tight relationship to the top and sides to create an end wall for casting the gel, screw means for removably attaching the gasketed end plate for easy insertion and removal, and a removable syringe holder selectively positioned on the top of the back cooling plate in the same position as the removable gasketed end plate, the syringe holder including a plurality of holes for holding syringes and directing the needles of the syringes to a predetermined point in the gel.

4. An apparatus as in claim 3 further comprising a cylindrical spacer for addition to the syringe holder to accommodate different size syringes.

* * * * *